United States Patent
Meier

(10) Patent No.: US 10,112,027 B2
(45) Date of Patent: Oct. 30, 2018

(54) APPARATUS FOR SUPPLYING RESPIRATORY GAS AND A METHOD FOR CONTROLLING THE APPARATUS

(71) Applicant: ResMed R&D Germany GmbH, Martinsried (DE)

(72) Inventor: Jörg Meier, Munich (DE)

(73) Assignee: ResMed R&D Germany GmbH, Martinsried (DE)

( * ) Notice: Subject to any disclaimer, the term of this patent is extended or adjusted under 35 U.S.C. 154(b) by 1076 days.

(21) Appl. No.: 14/185,966

(22) Filed: Feb. 21, 2014

(65) Prior Publication Data

US 2014/0166006 A1    Jun. 19, 2014

Related U.S. Application Data

(63) Continuation of application No. 13/112,592, filed on May 20, 2011, now Pat. No. 8,671,936, which is a (Continued)

(30) Foreign Application Priority Data

Aug. 20, 2001 (DE) .................................. 101 39 881

(51) Int. Cl.
  *A61M 16/16* (2006.01)
  *A61M 16/10* (2006.01)
(52) U.S. Cl.
  CPC .......... *A61M 16/16* (2013.01); *A61M 16/109* (2014.02); *A61M 16/161* (2014.02);
  (Continued)
(58) Field of Classification Search
  CPC .. A61M 11/005; A61M 11/04; A61M 11/041; A61M 11/042; A61M 2016/0039;
  (Continued)

(56) References Cited

U.S. PATENT DOCUMENTS

| 1,085,833 A | 2/1914 | Wilson |
| 2,840,682 A | 6/1958 | Rubenstein et al. |

(Continued)

FOREIGN PATENT DOCUMENTS

| AU | 14863/95 | 9/1995 |
| DE | 33 11 811 A1 | 10/1984 |

(Continued)

OTHER PUBLICATIONS

International Search Report dated Dec. 23, 2002 in International Appln. No. PCT/EP02/09147.

*Primary Examiner* — Gregory Anderson
*Assistant Examiner* — Margaret Luarca
(74) *Attorney, Agent, or Firm* — Nixon & Vanderhye P.C.

(57) ABSTRACT

An apparatus for supplying a respiratory gas includes a conveyor device for conveying the respiratory gas, a conduit for feeding the respiratory gas to a person, and a humidification device for humidifying the respiratory gas. A sensor device is configured to generate a signal indicative of the respiratory gas humidity and a control device is configured to control the humidification device with regard to the signal A method of supplying a respiratory gas to a patient, in which the respiratory gas is introduced by means of a conveyor device into the conduit leading to the patient and is humidified, includes operating the conveyor device so that a respiratory gas pressure which is above ambient pressure is provided in the conduit, and adjusting the humidity on the basis of signals indicative of the relative and/or absolute humidity of the respiratory gas generated by the sensor device.

19 Claims, 2 Drawing Sheets

Related U.S. Application Data continuation of application No. 12/394,615, filed on Feb. 27, 2009, now Pat. No. 7,997,270, which is a continuation of application No. 10/487,570, filed as application No. PCT/EP02/09147 on Aug. 15, 2002, now Pat. No. 7,516,740.

(52) U.S. Cl.
CPC ............... *A61M 2205/3368* (2013.01); *A61M 2205/3561* (2013.01); *A61M 2205/3584* (2013.01); *A61M 2230/205* (2013.01); *A61M 2230/432* (2013.01)

(58) Field of Classification Search
CPC .......... A61M 16/0066; A61M 16/0108; A61M 16/1085; A61M 16/109; A61M 16/1095; A61M 16/16; A61M 16/161; A61M 16/162; A61M 16/20; A61M 16/201; A61M 16/202; A61M 2205/3368; A61M 2205/3372; A61M 2205/3561; A61M 2205/3584; A61M 2205/362; A61M 2205/3653; A61M 2205/502; A61M 2230/205; A61M 2230/432; A61M 16/024; A62B 9/00; A62B 9/003
See application file for complete search history.

(56) References Cited

U.S. PATENT DOCUMENTS

| | | |
|---|---|---|
| 2,875,314 A | 2/1959 | Schreyer |
| 3,584,192 A | 6/1971 | Maag |
| 3,659,604 A | 5/1972 | Melville et al. |
| 3,871,373 A | 3/1975 | Jackson |
| 3,982,095 A | 9/1976 | Robinson |
| 3,987,133 A | 10/1976 | Andra |
| 4,014,382 A | 3/1977 | Heath |
| 4,038,980 A | 8/1977 | Fodor |
| 4,051,205 A | 9/1977 | Grant |
| 4,060,576 A | 11/1977 | Grant |
| 4,086,305 A | 4/1978 | Dobritz |
| 4,110,419 A | 8/1978 | Miller |
| 4,146,597 A | 3/1979 | Eckstein et al. |
| 4,152,379 A | 5/1979 | Suhr |
| 4,155,961 A | 5/1979 | Benthin |
| 4,201,204 A | 5/1980 | Rinne et al. |
| 4,203,027 A | 5/1980 | O'Hare et al. |
| 4,367,734 A | 1/1983 | Benthin |
| 4,430,994 A | 2/1984 | Clawson et al. |
| 4,532,088 A | 7/1985 | Miller |
| 4,561,287 A | 12/1985 | Rowland |
| 4,621,632 A | 11/1986 | Bartels et al. |
| 4,657,713 A | 4/1987 | Miller |
| 4,708,831 A | 11/1987 | Elsworth et al. |
| 4,753,758 A | 6/1988 | Miller |
| 4,829,998 A | 5/1989 | Jackson |
| 4,861,523 A | 8/1989 | Beran |
| 4,865,777 A | 9/1989 | Weiler et al. |
| 4,891,171 A | 1/1990 | Weiler et al. |
| 4,910,384 A | 3/1990 | Silver |
| 4,913,140 A | 4/1990 | Orec et al. |
| 4,921,642 A | 5/1990 | LaTorraca |
| 5,031,612 A | 7/1991 | Clementi |
| 5,062,145 A | 10/1991 | Zwaan et al. |
| 5,092,326 A | 3/1992 | Winn et al. |
| 5,163,423 A | 11/1992 | Suzuki |
| 5,231,979 A | 8/1993 | Rose et al. |
| 5,357,948 A | 10/1994 | Eilentropp |
| 5,367,604 A | 11/1994 | Murray |
| 5,368,786 A | 11/1994 | Dinauer et al. |
| 5,392,770 A | 2/1995 | Clawson et al. |
| 5,411,052 A | 5/1995 | Murray |
| 5,429,123 A * | 7/1995 | Shaffer ................. A61M 16/00 128/204.21 |
| 5,445,143 A | 8/1995 | Sims |
| 5,468,961 A | 11/1995 | Gradon et al. |
| 5,529,060 A | 6/1996 | Salmon et al. |
| 5,537,996 A | 7/1996 | McPhee |
| 5,537,997 A | 7/1996 | Mechlenburg et al. |
| 5,558,084 A | 9/1996 | Daniell et al. |
| 5,564,415 A | 10/1996 | Dobson et al. |
| 5,588,423 A | 12/1996 | Smith |
| 5,598,837 A | 2/1997 | Sirianne, Jr. et al. |
| 5,640,951 A | 6/1997 | Huddart et al. |
| 5,655,522 A | 8/1997 | Mechlenburg et al. |
| 5,673,687 A | 10/1997 | Dobson et al. |
| 5,694,923 A | 12/1997 | Hete et al. |
| 5,740,795 A | 4/1998 | Brydon |
| 5,769,071 A | 6/1998 | Turnbull |
| 5,800,741 A | 9/1998 | Glenn et al. |
| 5,845,636 A | 12/1998 | Gruenke et al. |
| 5,916,493 A | 6/1999 | Miller |
| 5,937,855 A | 8/1999 | Zdrojkowski et al. |
| 5,947,115 A | 9/1999 | Lordo et al. |
| 5,988,164 A | 11/1999 | Paluch |
| 6,010,118 A | 1/2000 | Milewicz |
| 6,017,315 A | 1/2000 | Starr et al. |
| 6,050,260 A | 4/2000 | Daniell et al. |
| 6,050,552 A | 4/2000 | Loescher et al. |
| 6,095,135 A | 8/2000 | Clawson et al. |
| 6,095,505 A | 8/2000 | Miller |
| 6,102,037 A * | 8/2000 | Koch ..................... A61M 16/16 128/201.13 |
| 6,116,029 A | 9/2000 | Krawec |
| 6,135,432 A | 10/2000 | Hebblewhite et al. |
| 6,201,223 B1 | 3/2001 | Nitta |
| 6,272,933 B1 | 8/2001 | Gradon et al. |
| 6,335,517 B1 | 1/2002 | Chauviaux et al. |
| 6,338,473 B1 | 1/2002 | Hebblewhite et al. |
| 6,349,722 B1 | 2/2002 | Gradon et al. |
| 6,349,724 B1 * | 2/2002 | Burton ............... A61M 16/0057 128/204.18 |
| 6,363,930 B1 | 4/2002 | Clawson et al. |
| 6,367,472 B1 | 4/2002 | Koch |
| 6,394,084 B1 | 5/2002 | Nitta |
| 6,398,197 B1 | 6/2002 | Dickinson et al. |
| 6,435,180 B1 | 8/2002 | Hewson et al. |
| 6,467,477 B1 | 10/2002 | Frank et al. |
| 6,470,885 B1 * | 10/2002 | Blue ...................... A61M 16/00 128/204.18 |
| 6,510,848 B1 | 1/2003 | Gibertoni |
| 6,520,021 B1 | 2/2003 | Wixey et al. |
| 6,523,810 B2 | 2/2003 | Offir et al. |
| 6,554,260 B1 | 4/2003 | Lipscombe et al. |
| 6,557,551 B2 | 5/2003 | Nitta |
| 6,584,972 B2 | 7/2003 | McPhee |
| 6,592,107 B1 | 7/2003 | Wong |
| 6,615,831 B1 | 9/2003 | Tuitt et al. |
| 6,629,934 B2 | 10/2003 | Mault et al. |
| 6,694,974 B1 | 2/2004 | George-Gradon et al. |
| 6,718,973 B2 | 4/2004 | Koch |
| 6,718,974 B1 | 4/2004 | Moberg |
| 6,772,999 B2 | 8/2004 | Lipscombe et al. |
| 6,802,314 B2 | 10/2004 | McPhee |
| 6,827,340 B2 | 12/2004 | Austin et al. |
| 6,877,510 B2 | 4/2005 | Nitta |
| 6,895,803 B2 | 5/2005 | Seakins et al. |
| 6,918,389 B2 | 7/2005 | Seakins et al. |
| 6,935,337 B2 | 8/2005 | Virr et al. |
| 7,043,979 B2 | 5/2006 | Smith et al. |
| 7,073,500 B2 | 7/2006 | Kates |
| 7,086,399 B2 | 8/2006 | Makinson et al. |
| 7,204,250 B1 * | 4/2007 | Burton ............... A61B 5/04085 128/205.23 |
| 7,306,205 B2 | 12/2007 | Huddart et al. |
| 7,413,173 B2 | 8/2008 | DiMatteo et al. |
| 7,478,635 B2 | 1/2009 | Wixey et al. |
| 2001/0029340 A1 | 10/2001 | Mault et al. |
| 2002/0013536 A1 | 1/2002 | Mault |
| 2002/0104536 A1 * | 8/2002 | Richey, II ........... A61M 16/024 128/204.22 |
| 2002/0112725 A1 | 8/2002 | Thudor et al. |
| 2004/0074493 A1 | 4/2004 | Seakins et al. |

(56) References Cited

U.S. PATENT DOCUMENTS

| | | |
|---|---|---|
| 2004/0079370 A1 | 4/2004 | Gradon et al. |
| 2004/0102731 A1 | 5/2004 | Blackhurst et al. |
| 2004/0221844 A1 | 11/2004 | Hunt et al. |
| 2006/0137445 A1 | 6/2006 | Smith et al. |
| 2006/0191531 A1 | 8/2006 | Mayer et al. |
| 2006/0213515 A1 | 9/2006 | Bremner et al. |
| 2006/0272639 A1 | 12/2006 | Makinson et al. |
| 2007/0079826 A1 | 4/2007 | Kramer et al. |
| 2007/0230927 A1 | 10/2007 | Kramer |
| 2007/0284361 A1 | 12/2007 | Nadjafizadeh et al. |
| 2008/0072900 A1 | 3/2008 | Kenyon et al. |
| 2008/0105257 A1 | 5/2008 | Klasek et al. |
| 2008/0302361 A1 | 12/2008 | Snow et al. |
| 2011/0220105 A1 | 9/2011 | Meier |

FOREIGN PATENT DOCUMENTS

| | | |
|---|---|---|
| DE | 36 29 353 C1 | 1/1988 |
| DE | 40 34 611 A1 | 5/1992 |
| DE | 94 09 231 U1 | 12/1994 |
| DE | 196 02 077 A | 8/1996 |
| DE | 199 28 003 A | 12/2000 |
| EP | 1 005 878 A | 6/2000 |
| EP | 1 479 404 A2 | 11/2004 |
| EP | 1 491 226 B1 | 1/2006 |
| EP | 1 197 237 B1 | 1/2007 |
| GB | 2 277 689 A | 11/1994 |
| GB | 2 338 420 A | 12/1999 |
| JP | 5-317428 A | 12/1993 |
| JP | 8-61731 A | 3/1996 |
| JP | 9-234247 A | 9/1997 |
| SU | 379270 | 4/1973 |
| WO | WO 98/04311 A1 | 2/1998 |
| WO | WO 00/07498 | 2/2000 |
| WO | WO 00/21602 A1 | 4/2000 |
| WO | WO 01/13981 A1 | 3/2001 |
| WO | WO 01/56454 A | 8/2001 |
| WO | WO 2004/039444 A1 | 5/2004 |
| WO | WO 2005/079898 A2 | 9/2005 |
| WO | WO 2008/148154 A1 | 12/2008 |
| WO | WO 2009/015410 A1 | 2/2009 |

\* cited by examiner

APPARATUS FOR SUPPLYING RESPIRATORY GAS AND A METHOD FOR CONTROLLING THE APPARATUS

CROSS-REFERENCES TO RELATED APPLICATIONS

This application is a continuation of U.S. application Ser. No. 13/112,592, filed May 20, 2011, now U.S. Pat. No. 8,671,936, which is a continuation of U.S. application Ser. No. 12/394,615, filed Feb. 27, 2009, now U.S. Pat. No. 7,997,270, which is a continuation of U.S. application Ser. No. 10/487,570, filed Feb. 20, 2004, now U.S. Pat. No. 7,516,740, which is the U.S. national phase of International Application PCT/EP02/09147, filed Aug. 15, 2002 which designated the U.S. and claims priority to German Application No. 101 39 881.6, filed Aug. 20, 2001, the entire contents of each of which are hereby incorporated by reference.

FIELD OF THE INVENTION

The invention concerns an apparatus for supplying a respiratory gas and a method of controlling the apparatus.

BACKGROUND OF THE INVENTION

In particular for the treatment of sleep-related breathing disorders, it is possible to supply the patient with a respiratory gas, for example filtered ambient air, at a pressure which is increased in relation to the ambient pressure. A respiratory gas pressure which is in the range of between 4 and 18 mbar above the ambient pressure makes it possible to obviate obstructions in the region of the upper respiratory tracts.

It is possible for the pressure of the respiratory gas to be definedly varied. Thus it is possible in particular to control the pressure in such a way that lower respiratory gas pressures obtained during the expiration phases than during the inspiration phases. It is further possible to adapt the respiratory gas pressure in such a way that for example an increased respiratory gas pressure is only set when the person to whom artificial respiration is to be given is in a predetermined stage in sleep. It is further possible for the respiratory gas supplied to the patient to be charged with selected additive substances and, in particular, humidified. Humidification of the respiratory gas can be effected by the gas being brought into contact with warmed water. The degree of humidification of the respiratory gas can be adjusted in that case by way of the temperature of the humidifying water.

SUMMARY OF THE INVENTION

The object of the invention is to provide an apparatus for and a method of supplying a respiratory gas to a breathing person, whereby improved physiological compatibility of the supply of respiratory gas is achieved.

According to the invention that object is attained by an apparatus having the features including a conveyor device for conveying the respiratory gas, a conduit for feeding the respiratory gas conveyed by the conveyor device to a person, a humidification device for humidifying the respiratory gas, a sensor device for generating a signal indicative in respect of the respiratory gas humidity and a control device for controlling the humidification device having regard to the signal which is generated by the sensor device and which is indicative in respect of the respiratory gas humidity.

In that way it is advantageously possible to match the humidity state of the respiratory gas in a narrow tolerance range to the instantaneous physiological demands of the patient. In that way it is advantageously possible to ensure that the respiratory gas is not inadequately or excessively humidified by virtue of an adjustment which is initially implemented on the part of the patient in the context of a deep-sleep phase or upon a change in breathing characteristic.

In accordance with a particularly preferred embodiment of the invention the sensor device for generating a signal indicative in respect of the absolute and/or relative humidity of the respiratory gas is arranged in the region of a breathing mask provided for supplying the respiratory gas.

Alternatively thereto or in a particularly advantageous manner in combination with that feature it is also possible for a sensor device for producing a signal indicative in respect of the humidity state of the respiratory gas to be arranged at the outlet of an air humidification device. By virtue of combined consideration of an air humidity signal generated in the outlet region of an air humidification device and an air humidity signal generated in the region of the patient or mask, it is then possible to check whether an unacceptably great change in the humidity state of the respiratory gas and in particular precipitation of water takes place in the region of a respiratory gas conduit means provided between the breathing mask and the air humidification device.

It is also possible, for example by a temperature detection device provided in the region of the breathing mask, to detect the temperature of the respiratory gas in the region of the patient and, on the basis of an additional humidity signal produced for example in the region of an air humidification device, to assess whether an unacceptably high relative humidity level obtains in the respiratory gas in the region near the patient. Particularly in conjunction with a sensor device provided in the region of the patient for detecting a signal indicative in respect of the humidity state of the respiratory gas, it is advantageously possible to draw a distinction between expiratory humidity states and inspiratory humidity states.

The humidity states ascertained for the respective breathing phases can be taken into consideration in terms of regulating the respiratory gas humidity level, on the basis of a predetermined or preferably adaptively matched regulating procedure.

By virtue of the present invention it is possible to reduce the proportion of water which is entrained in drop form in the respiratory gas. That reliably avoids any germs being transported by way of drops of water.

In accordance with a particularly preferred embodiment of the invention the sensor device is arranged in the region, near a patient, of a respiratory gas conduit system. In that way it is advantageously possible to detect the respiratory gas humidity state which is actually relevant to the user. In that respect, in a particularly advantageous configuration, the sensor device is arranged in the region of a breathing mask and in particular is integrated into the breathing mask. In that respect the sensor device is preferably of such a design configuration that the measurement dynamics thereof are considerably higher than the breathing rate of the patient. In that way it is possible to specifically detect the humidity state of the respiratory gas for the respective breathing phases. The measurement values which are detected in that way for the expiration phase and for the inspiration phase, in regard to respiratory gas humidity level, can be evaluated by a preferably adaptively optimized regulating procedure. It is possible to disregard the respiratory gas humidity values ascertained in respect of the expiration phase or to take them into account only as control values, and to implement adjustment of the respiratory gas humidity essentially having regard to the respiratory gas humidity values detected in respect of the inspiration processes.

As an alternative to arranging the sensor device in the region near the patient—or in a particularly advantageous fashion in combination therewith—it is possible for the sensor device or a further sensor device to be arranged in the region between the breathing mask and a hose conduit portion, and in particular to integrate it into a coupling structure or a washing-out valve arrangement.

The sensor device can also be arranged in the region of the humidification device so that the humidity state of the respiratory gas can be directly detected by way of the sensor device and the operating performance of the humidification device can be matched in regard to a desired respiratory gas reference humidity state, having regard to the instantaneous respiratory gas humidity level.

In accordance with a particularly preferred embodiment of the invention the sensor device includes an electrical sensor element, wherein provided in the region of that sensor element is an electronic circuit, for the generation of a data sequence, by way of which the respiratory gas humidity measurement signals detected on the part of the sensor element can be transmitted in encoded form. Processing of the respiratory gas humidity signals detected by the sensor element in the region of the sensor element itself makes it possible substantially to avoid falsification of the signal, for example because of the transmission properties of any signal lines.

The sensor element is preferably designed in such a way that it detects the respiratory gas humidity on the basis of inductive, capacitive and/or thermal interaction effects. As an alternative thereto or also in combination with the use of physical measurement principles of that kind, it is also possible to detect the respiratory gas humidity by optical means.

In accordance with a particularly preferred embodiment of the invention a signal indicative in respect of the temperature of the respiratory gas is also generated on the part of the sensor device. Insofar as that is not the case, it is possible for a measuring device which is suitable for detecting the temperature of the respiratory gas to be preferably also arranged in the immediate proximity of the sensor element.

It is possible for the sensor device for detecting the respiratory gas humidity to be arranged in the region of the humidification device and for a temperature detection device to be provided in the region near the patient. On the basis of the respiratory gas humidity state detected in the region of the humidification device and the respiratory gas temperature detected in the region of the patient, it is possible to detect the relative humidity level of the respiratory gas at the patient. The measurement values detected on the part of the temperature detection device or also the humidity sensor device can also be taken into consideration in actuation of the conveyor device, besides actuation of the humidification device. Thus, on the basis of the measurement values generated by the humidity sensor device and/or the temperature detection device, it is possible to implement a breathing phase recognition operation and to modulate the respiratory gas pressure in accordance with the recognized breathing phases.

The operation of ascertaining a reference respiratory gas humidity value which is relevant for operation of the humidification device is preferably effected having regard to a data set, in particular an adaptively optimized data field, which takes account of the sleep state of the patient, the breath volume of the patient and for example also the position of sleep of the patient, and in particular the degree of neck rotation thereof. Thus it is possible for example, in periods of time in which the patient is sleeping on one side, to actuate lower respiratory gas humidity levels than for example in a situation involving a supply of respiratory gas when lying on the back.

Adjustment of the humidification output of the humidification device, such adjustment being effected in accordance with the signals generated by the humidity sensor device, is effected preferably by altering the temperature of the humidification water which comes into contact with the respiratory gas.

As an alternative to or also in combination with the above-described measure it is also possible to alter the humidification output of the humidification device for example by altering the effective water surface area available for humidification purposes. It is also possible for the respiratory gas temperature and in particular the temperature of the respiratory gas to be definedly adjusted before it comes into contact with the humidification water.

It is also possible to alter the flow characteristic of the air coming into contact with the humidification water, in such a way that the respectively desired respiratory gas humidity values checked by the sensor device occur at the outlet of the humidification device.

An embodiment of the invention, which is advantageous in regard to particularly precise conditioning of the respiratory gas in respect of the moisture contained therein is afforded if, if necessary, only a partial flow of the respiratory gas is brought into contact with the humidification water, wherein the respiratory gas humidity level is determined by way of the ratio of the partial flow of respiratory gas which has come into contact with the humidification water, and the partial flow of respiratory gas which is taken past the humidification device. It is possible for the conduit means to be passed through the humidification device in such a way that a respiratory gas which is pushed back over the humidification device during an expiration phase does not come into contact with the humidification water.

An embodiment of the invention, which is advantageous in regard to a particularly high level of handling comfort, is provided in that, disposed in the region of the sensor device for detecting the respiratory gas humidity is a transmitting device for wireless transmission of the data sequence generated in respect of the respiratory gas humidity. A transmitting device of that kind can be for example in the form of a blue tooth transmitting device. It is also possible for the signals generated on the part of the sensor device to be transmitted back to the humidification device optically, in particular in the form of infrared signals. When using a respiratory gas conduit produced from a material which is transparent at least in the infrared range, it is possible for the respiratory gas hose conduit to be used as an optical waveguide, by way of which the signals generated on the part of the sensor device can be transmitted to the humidification device or to a control device provided for controlling the humidification device.

The object of the invention as specified in the opening part of this specification is further attained in accordance with the invention by a method of supplying a respiratory gas to a patient, in which the respiratory gas is introduced by means of a conveyor device into a conduit system leading to a patient and is humidified, wherein the conveyor device is operated in such a way that a respiratory gas pressure which is above ambient pressure at least in phase-wise manner obtains in the air conduit system, wherein signals indicative in respect of the relative and/or absolute humidity of the respiratory gas are generated by means of a sensor device and the humidity of the respiratory gas is adjusted on the basis of the signals generated in that way.

In accordance with a particularly preferred embodiment of this method the humidity of the respiratory gas is detected in the region near the patient, in particular in the region of a breathing mask. In that way it is in particular possible to detect the respiratory gas humidity level both for the expiration phases and also for the inspiration phases and to take account of the measurement values individually obtained in that way, in ascertaining a reference respiratory gas humidity value.

The method according to the invention and also the above-described apparatus are particularly advantageously suitable for the artificial respiratory and breathing therapy sector. Humidification of the respiratory gas can also be effected in particular by ultrasonic atomizers, bubble vaporizers, surface contact humidifiers and injection systems. The dynamics of the respiratory gas humidification operation is preferably selected to be so high that in particular unacceptably high or also unacceptably low respiratory gas humidity values can be sufficiently quickly adjusted.

In regard to regulation of the respiratory gas temperature and/or the respiratory gas humidity content, preferably the following control parameters (X) are evaluated: the respiratory gas volume flow, the respiratory gas temperature, the humidity content of the respiratory gas in terms of relative and/or absolute humidity, levels of gas concentration, in particular $CO_2$ saturation, the therapy pressure and/or the mask pressure and/or the difference between a therapy reference pressure and the mask pressure actually occurring at the patient, polysomnographic parameters such as snoring, heart rate, oxygen saturation, body position; and ambient conditions such as air pressure, temperature and humidity and preferably also EEG-signals, in particular measurement values which are derived therefrom and are indicative in respect of the sleep phase.

The respiratory gas temperature and/or the respiratory gas humidity can be adjusted by way of the water surface area (preferably by varying the effective water surface area in the air humidifier) and/or the amount of water (preferably by means of the amount of water in the air humidifier) and/or the water temperature (preferably by heating or cooling the water and/or water molecules in the air) and/or the respiratory gas temperature (preferably by heating or cooling the respiratory air) and/or the mixing of gases (preferably by mixing various gases, for example dry air with mist of high humidity or also by mixing gas flows involving differing temperatures and/or air humidity levels and also by variable flow resistances in the region of the air humidifier.

Further details of the invention will be apparent from the description hereinafter with reference to the drawings in which:

DETAILED DESCRIPTION OF THE INVENTION

Figure 1:
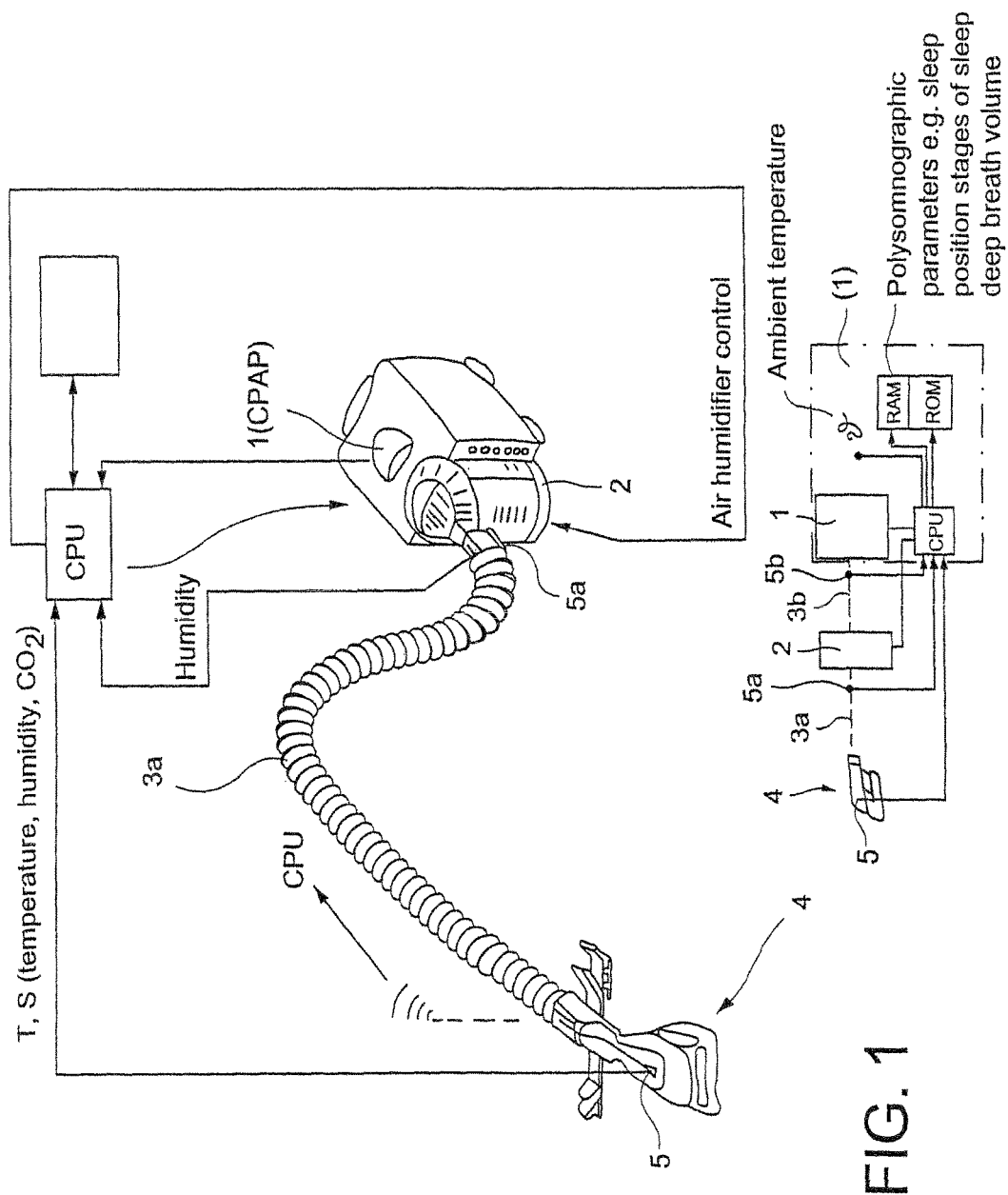
FIG. 1 is a simplified diagrammatic view to illustrate the structure of an apparatus according to the invention.

The system shown in FIG. 1 for supplying a respiratory gas includes a respiratory gas conveyor device 1, a respiratory gas humidification device 2 coupled thereto, and a breathing mask device 4 coupled to the respiratory gas humidification device 2 by way of a flexible hose conduit 3a.

The respiratory gas humidification device 2 can also be coupled in the form of what is known as a stand-alone unit to the respiratory gas conveyor device 1 by way of a preferably flexible hose conduit 3b. As an alternative thereto it is also possible for the respiratory gas humidification device 2 and the respiratory gas conveyor device 1 to be combined together to form an integral unit.

Disposed in the region of the conduit system which is provided to convey the respiratory gas and which is formed by the respiratory gas conveyor device 1, optionally the flexible hose conduit 3b, the respiratory gas humidification device 2, the flexible hose conduit 3a and in particular also the breathing mask device 4, there is at least one sensor device for detecting the humidity state of the respiratory gas being conveyed. In the embodiment illustrated here, provided in particular in the region of the breathing mask device 4 is a humidity sensor 5, by way of which a signal indicative in respect of the respiratory gas humidity state is generated and passed to a control device CPU. The control device CPU can either be arranged in the region of the humidity sensor 5 or can preferably be integrated into the respiratory gas humidification device or the respiratory gas conveyor device 1.

The respiratory gas humidification device 2 can be actuated on the basis of the signals generated on the part of the humidity sensor 5, in such a way that the humidity state of the respiratory gas which is humidified in the respiratory gas humidification device 2 takes account, in a close tolerance range, of the instantaneous physiological needs of the person being afforded respiration by way of the breathing mask device 4.

In determining the reference respiratory gas humidity state which is decisive at the present time, besides the signals generated by the humidity sensor 5, the procedure preferably also takes account of a performance graph or array which for example takes account of further polysomnographic parameters such as for example the degree of oxygen saturation of the blood of the person to whom respiration is being administered, noises, in particular snoring events as well as the heart rate and the instantaneous breathing characteristic. It is also possible, when calculating the reference humidity state of the respiratory gas, to take account of stages in sleep, ambient conditions as well as other physiological parameters, in particular the position in which the patient sleeps.

The system illustrated here has further sensor devices 5a, 5b by which signals are generated, used for defined conditioning of the respiratory gas. The sensor device 5b involves a sensor device for generating signals indicative in respect of the respiratory gas temperature: by taking account of the respiratory gas temperature signal generated on the part of the sensor device 5b, it is possible definedly to adapt the humidification output of the humidification device, as is required to achieve a desired reference humidity state.

It is possible by means of the sensor 5a provided in the region of the humidification device 2 to detect the humidity state of the respiratory gas immediately after it has been charged with water.

By taking account of the signal generated by the sensor device 5a disposed in the ambient region of the respiratory gas humidification device and also the signal generated by the sensor device 5 in the region near the mask, it is then possible to recognize any changes in state of the respiratory gas, caused by the flexible hose conduit 3a, in particular the formation of condensation water in the flexible hose conduit 3a, and on the basis thereof to implement corrections to the humidification output of the respiratory gas humidification device 2.

The sensor device 5 provided in the region of the breathing mask device 4 preferably includes a sensor element for detecting the humidity state on the basis of electromagnetic interactions, in particular capacitive interactions. The measurement signals generated by the sensor element are preferably converted into a digital data format by a connected measurement circuit while still in the region of the sensor element, and transmitted to the CPU by way of a preferably potential-free measurement data output.

It is possible for transmission of the humidity signals generated in the region of the breathing mask to be implemented by way of a data line which is preferably integrated into the flexible hose conduit 3a or is at least guided along same.

As an alternative thereto it is also possible for the measurement signals generated on the part of the humidity sensor 5 to be transmitted wirelessly, for example by way of a blue tooth arrangement, to the CPU or also to other detection devices. In this case the voltage supply for the humidity sensor 5 is preferably effected by means of a voltage source provided in the region of the breathing mask device 4, for example in the form of a button cell or a solar cell.

The respiratory gas humidification device 2 may include for example an ultrasonic atomizing device, a bubble vaporizer or a surface contact humidifier. Preferably the humidification output of the humidification device 2 can be matched to the required humidification output within a time window which does not exceed a duration of 10 minutes.

Figure 2:
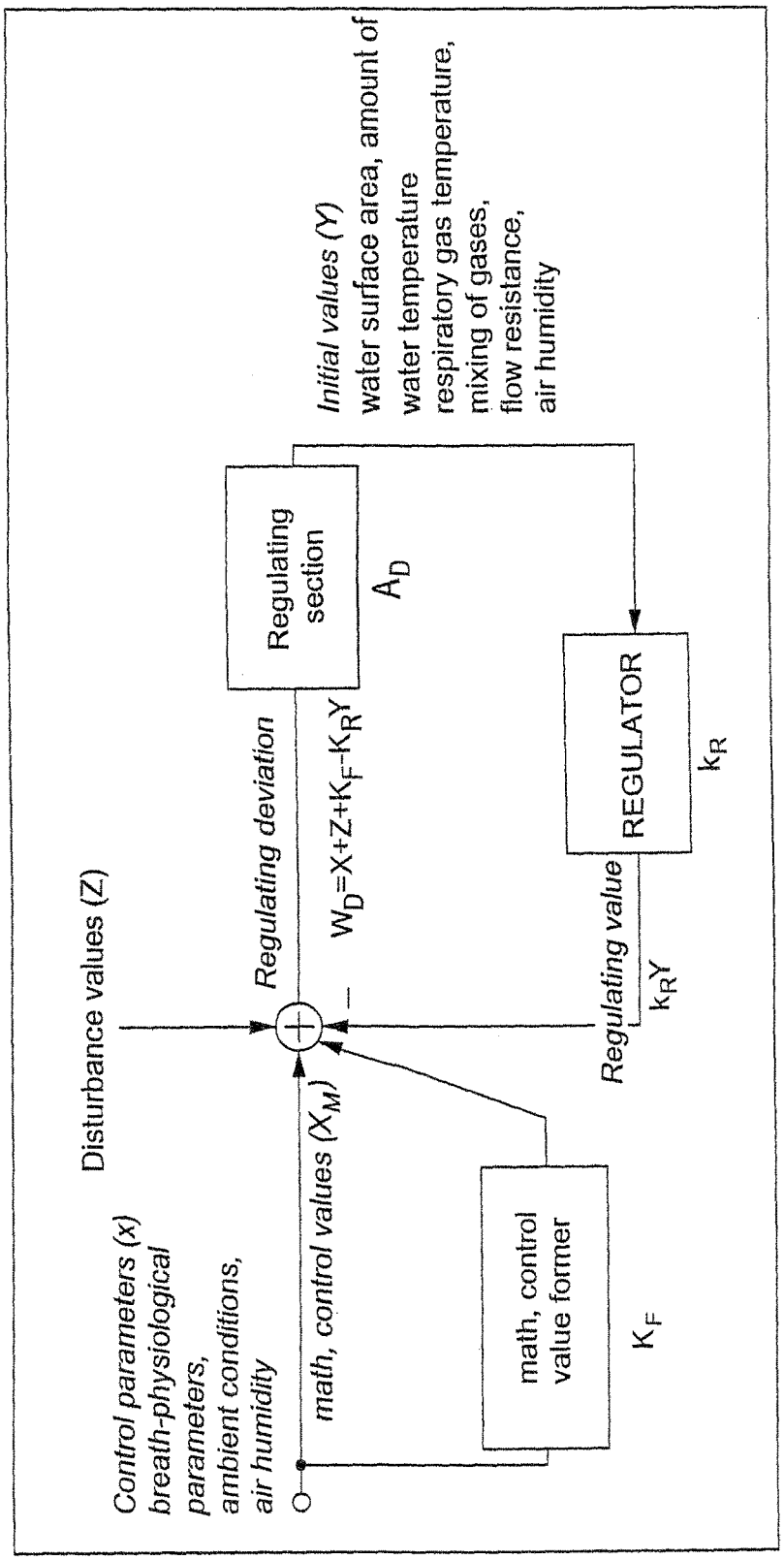
FIG. 2 shows a regulating circuit according to the invention for adjusting the respiratory gas humidity level.

FIG. 2 diagrammatically shows a preferred embodiment of a regulating circuit for controlling the humidity state of the respiratory gas. That regulating circuit makes it possible to individually match the respiratory gas temperature and/or the respiratory gas air humidity to the instantaneous physiological state of the patient, that is to say to increase it or reduce it in phase-wise manner.

Preferably the following control parameters (X) are evaluated for the purposes of regulating the respiratory gas state:
volume flow;
respiratory gas temperature;
humidity content of the respiratory air in terms of relative and/or absolute humidity;
levels of gas concentration (gas composition, in particular $0_2$ content);
therapy pressure and/or mask pressure and/or delta between therapy pressure and the actually applied mask pressure;
polysomnographic parameters such as snoring, heart rate, oxygen saturation, body position;
ambient conditions such as air pressure, temperature and humidity content;
EEG (sleep phase such as NREM 1-4, REM);
mathematical control values ($X_M$);
mathematical calculations from the control parameters.

Preferably the following initial parameters (Y) are regulated for the respiratory gas temperature and/or respiratory gas humidity:
water surface area (preferably by altering the effective water surface area in the air humidifier); and/or
amount of water (preferably by way of the amount of water which is in the air humidifier); and/or
water temperature (preferably by heating or cooling the water and/or water molecules in the air); and/or
respiratory gas temperature (preferably by heating or cooling the respiratory air); and/or
mixing gases (preferably by mixing various gases, for example dry air with mist/of high humidity at differing temperatures and/or with differing air humidity); and/or
flow resistances (preferably by way of the flow speed in the system).

The evaluation operation is preferably effected on the basis of the evaluation algorithm described hereinafter:

1st Feature

At least one control parameter (X) or a suitable combination is required for regulating the respiratory temperature and/or the respiratory humidity.

2nd Feature

The control parameters are evaluated over a given time interval, preferably over the expiration and inspiration time. The measurement values obtained in that way, within an interval, are subjected to further mathematical calculation, preferably maxima and/or minima and/or delta between minimum and maximum and/or mean values.

3rd Feature

Typical behavior patterns on the part of the patients can be calculated from the control parameters (X). Thus, it is possible to establish the instantaneous breathing state by virtue of the reverse correlation of given control parameters (X), for example volume flow, temperature fluctuation in the respiration air, that is to say it is possible to draw a distinction between stable respiration (uniform amplitudes and regular respiration rate) and unstable respiration (irregular amplitude and respiration rate, periodic respiration) and regulation can be implemented on the basis of the mathematical control values ($X_M$).

The mode of operation of a respiratory gas supply system according to the invention is described hereinafter.

Control Parameters:

Volume Flow:

1. If the measured volume flow exceeds a limit value (for example due to mouth leakage), an increase in the respiratory gas temperature or an increase in respiration humidity is preferably effected. If the measured volume flow falls below a limit value (for example due to a low breath volume), cooling of the respiratory gas temperature or a reduction in respiration humidity is preferably effected.

2. A distinction can be made between stable respiration (uniform amplitude and regular respiration rate) and unstable respiration (irregular amplitude and respiration rate, periodic respiration) preferably by reverse correlation from the volume flow. The respiratory gas temperature and the respiration humidity is regulated by the result of the reverse correlation.

Respiratory Gas Temperature:

1. If the measured respiratory gas temperature falls below a limit value (for example due to mouth leakage), an increase in the respiratory gas temperature or an increase in respiratory gas humidity is preferably effected. If the measured respiratory gas temperature exceeds a limit value (for example due to a low breath volume), cooling of the respiratory gas temperature or a reduction in respiration humidity is preferably effected.

2. Both the temperature fluctuations during inspiration and expiration can be evaluated. The temperature difference measured from breathing in and breathing out is used as a regulating parameter. In the case of big breaths (large volume flow) the temperature delta between inspiration and expiration is highly pronounced so that preferably the respiratory gas temperature or respiration humidity is increased.

3. A distinction can be made between stable respiration (uniform amplitude and regular respiration rate) and unstable respiration (irregular amplitude and respiration rate, periodic respiration) preferably by reverse correlation from the respiratory gas temperature. The respiratory gas temperature and the respiration gas humidity are regulated by the result of the reverse correlation.

Humidity:

The respiratory air humidity is measured during expiration and inspiration. Humidity measurement can be effected both relatively and also absolutely.

1. The expiration and inspiration measurement values obtained in that way are further mathematically calculated, preferably over a time interval in which the minimum and/or the maximum and/or the delta between minimum and maximum and/or the mean value is formed.

2. The control parameter humidity can also be combined for example in dependence with the ambient temperature, kind of respiration (reverse correlation).

Initial Parameters:

Gas Concentration:

1. The respiratory gas humidity and/or the respiratory gas temperature can be regulated by mixing dry and humid air. Thus it is possible to branch off the air flow so that the air is passed over the surface of the water and/or over the cooling/heating means.

Flow Resistance:

1. The flow resistance within the air humidifier can be altered. If for example a high level of air humidity is required then contact or the residence time in the humidifier can be increased by increasing the flow resistance in the air humidifier.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An apparatus configured to deliver a flow of breathable gas at a continuously positive pressure with respect to ambient air pressure to an entrance of a patient's airways including at least an entrance of the patient's nares throughout the patient's respiratory cycle while the patient is sleeping to ameliorate sleep disordered breathing, the apparatus comprising:
a blower configured to positively pressurize the breathable gas to a predetermined level;
a humidifier configured to humidify the breathable gas; and
a controller configured to (1) distinguish between the patient's expiratory breathing phase and the patient's inspiratory breathing phase based on at least one breathable gas control parameter evaluated during the patient's expiratory breathing phase and the patient's inspiratory breathing phase and (2) regulate humidity of the breathable gas as a function of at least one measured inspiratory value of the at least one breathable gas control parameter, the at least one measured inspiratory value corresponding to the patient's inspiratory breathing phase,
wherein the controller is configured to disregard measured expiratory values associated with the at least one breathable gas control parameter when regulating the humidity of the breathable gas, the measured expiratory values corresponding to the patient's expiratory breathing phase.

2. The apparatus of claim 1, wherein the controller is configured to evaluate the at least one breathable gas control parameter over a predetermined time interval that includes at least one cycle of the patient's inspiratory breathing phase and the patient's expiratory breathing phase.

3. The apparatus of claim 2 further comprising a patient interface configured to sealingly engage the patient's face and deliver the humidified breathable gas from the humidifier to the patient's airways, wherein the at least one breathable gas control parameter includes at least one of: volume flow of the breathable gas, temperature of the breathable gas, humidity of the breathable gas, concentration levels of the breathable gas, a predetermined therapy pressure, pressure of the breathable gas at the patient interface, a difference between the predetermined therapy pressure and the pressure of the breathable gas at the patient interface, polysomnographic parameters of the patient, ambient conditions, sleep phase, and mathematical control values.

4. The apparatus of claim 3, wherein the polysomnographic parameters include at least one of: snoring, heart rate oxygen saturation, body position and neck position.

5. The apparatus of claim 3, wherein the ambient conditions include at least one of: air pressure, temperature and humidity.

6. A CPAP system configured to deliver a flow of breathable gas at a continuously positive pressure with respect to ambient air pressure to an entrance of a patient's airways including at least an entrance of the patient's nares throughout the patient's respiratory cycle while the patient is sleeping to ameliorate sleep disordered breathing, the CPAP system comprising:
the apparatus of claim 1;
a patient interface configured to sealingly engage an area adjacent the entrance to the patient's airways; and
an air circuit configured to deliver the breathable gas to the patient interface.

7. The CPAP system of claim 6, further comprising a sensing device positioned at the patient interface and in communication with the controller of the apparatus, the sensing device being configured to sense at least one of humidity and temperature of the breathable gas.

8. A method for delivering a flow of breathable gas at a continuously positive pressure with respect to ambient air pressure to an entrance of a patient's airways including at least an entrance of the patient's nares throughout the patient's respiratory cycle while the patient is sleeping to ameliorate sleep disordered breathing, the method comprising:
positively pressurizing the breathable gas to a predetermined level;
distinguishing between the patient's expiratory breathing phase and the patient's inspiratory breathing phase based on at least one breathable gas control parameter evaluated during the patient's expiratory breathing phase and the patient's inspiratory breathing phase;
regulating humidity of the breathable gas as a function of at least one measured inspiratory value of the at least one breathable gas control parameter, the at least one measured inspiratory value corresponding to the patient's inspiratory breathing phase; and delivering the breathable gas to the patient, wherein measured expiratory values associated with the at least one breathable gas control parameter are disregarded when regulating the humidity of the breathable gas, the measured expiratory values corresponding to the patient's expiratory breathing phase.

9. The method of claim 8, wherein the at least one breathable gas control parameter is evaluated over a predetermined time interval that includes at least one cycle of the patient's inspiratory breathing phase and the patient's expiratory breathing phase.

10. The method of claim 9, wherein the at least one breathable gas control parameter includes at least one of: volume flow of the breathable gas, temperature of the breathable gas, humidity of the breathable gas, concentration levels of the breathable gas, a predetermined therapy pressure, pressure of the breathable gas at a patient interface, a difference between the predetermined therapy pressure and the pressure of the breathable gas at the patient interface, polysomnographic parameters of the patient, ambient conditions, sleep phase, and mathematical control values.

11. The method of claim 10, wherein the polysomnographic parameters include at least one of: snoring, heart rate oxygen saturation, body position and neck position.

12. The method of claim 10, wherein the ambient conditions include at least one of: air pressure, temperature and humidity.

13. An apparatus configured to deliver a flow of breathable gas at a continuously positive pressure with respect to ambient air pressure to an entrance of a patient's airways including at least an entrance of the patient's nares throughout the patient's respiratory cycle while the patient is sleeping to ameliorate sleep disordered breathing, the apparatus comprising:

a blower configured to positively pressurize the breathable gas to a predetermined level;

a humidifier configured to humidify the breathable gas;

a sensing device configured to sense humidity of the pressurized breathable gas; and a controller configured to (1) distinguish between the patient's expiratory humidity state and the patient's inspiratory humidity state based on humidity values sensed by the sensing device during the patient's inspiratory and expiratory breathing phases and (2) regulate humidity of the pressurized breathable gas based on the inspiratory humidity state, wherein the controller is configured to disregard the humidity values sensed by the sensing device during the patient's expiratory breathing phase when regulating the humidity of the breathable gas.

14. The apparatus of claim 13, wherein the controller is configured to distinguish between the patient's expiratory and inspiratory humidity states based on maxima and/or minima humidity levels sensed by the sensing device.

15. The apparatus of claim 13 further comprising a patient interface configured to sealingly engage the patient's face and deliver the humidified breathable gas from the humidifier to the patient's airways, wherein the controller is configured to determine the expiratory humidity state and the inspiratory humidity state based on at least one breathable gas control parameter, the at least one breathable gas control parameter including at least one of: volume flow of the breathable gas, temperature of the breathable gas, humidity of the breathable gas, concentration levels of the breathable gas, a predetermined therapy pressure, pressure of the breathable gas at the patient interface, a difference between the predetermined therapy pressure and the pressure of the breathable gas at the patient interface, polysomnographic parameters of the patient, ambient conditions, sleep phase, and mathematical control values.

16. The apparatus of claim 15, wherein the polysomnographic parameters include at least one of: snoring, heart rate oxygen saturation, body position and neck position.

17. The apparatus of claim 15, wherein the ambient conditions include at least one of: air pressure, temperature and humidity.

18. A CPAP system configured to deliver a flow of breathable gas at a continuously positive pressure with respect to ambient air pressure to an entrance of a patient's airways including at least an entrance of the patient's nares throughout the patient's respiratory cycle while the patient is sleeping to ameliorate sleep disordered breathing, the CPAP system comprising:

the apparatus of claim 13;

a patient interface configured to sealingly engage an area adjacent the entrance to the patient's airways; and an air circuit configured to deliver the breathable gas to the patient interface.

19. The CPAP system of claim 18, wherein the sensing device is positioned at the patient interface.

* * * * *